(12) United States Patent
Esposito et al.

(10) Patent No.: US 10,849,425 B2
(45) Date of Patent: Dec. 1, 2020

(54) MOTORIZED MODULAR SMART SHELVING AND STORAGE UNIT

(71) Applicant: The Intellectual Property Network, Inc., Tucson, AZ (US)

(72) Inventors: Mary Pat Esposito, Bristol, IL (US); John Esposito, New River, AZ (US); Ron Esposito, Bristol, IL (US)

( * ) Notice: Subject to any disclaimer, the term of this patent is extended or adjusted under 35 U.S.C. 154(b) by 0 days.

(21) Appl. No.: 16/153,625

(22) Filed: Oct. 5, 2018

(65) Prior Publication Data

US 2019/0104843 A1  Apr. 11, 2019

Related U.S. Application Data

(60) Provisional application No. 62/569,335, filed on Oct. 6, 2017.

(51) Int. Cl.
| | |
|---|---|
| *A47B 47/00* | (2006.01) |
| *A47B 96/02* | (2006.01) |
| *A47B 51/00* | (2006.01) |
| *A47B 88/457* | (2017.01) |
| *A47B 46/00* | (2006.01) |
| *G16H 40/67* | (2018.01) |
| *G16H 20/13* | (2018.01) |
| *G06F 19/00* | (2018.01) |

(52) U.S. Cl.
CPC ......... *A47B 47/0091* (2013.01); *A47B 46/00* (2013.01); *A47B 51/00* (2013.01); *A47B 88/457* (2017.01); *A47B 96/025* (2013.01); *G06F 19/00* (2013.01); *A47B 2220/0061* (2013.01); *A47B 2220/0091* (2013.01); *G16H 20/13* (2018.01); *G16H 40/67* (2018.01)

(58) Field of Classification Search
None
See application file for complete search history.

(56) References Cited

U.S. PATENT DOCUMENTS

| | | | |
|---|---|---|---|
| 4,102,275 | A | 7/1978 | Spound et al. |
| 4,523,526 | A | 6/1985 | O'Neill |
| 4,664,230 | A | 5/1987 | Olsen |
| 5,086,593 | A | 2/1992 | Walentine |
| 5,195,642 | A | 3/1993 | Dardashti |
| 5,273,352 | A | 12/1993 | Saper |
| 5,421,467 | A | 6/1995 | Dittborn |
| 5,515,239 | A | 5/1996 | Kamerman et al. |
| 5,577,620 | A | 11/1996 | Jacob |
| 5,586,816 | A | 12/1996 | Geiss |
| 5,992,647 | A | 11/1999 | Malik |

(Continued)

FOREIGN PATENT DOCUMENTS

| | | |
|---|---|---|
| AU | 2016100051 | 2/2016 |
| EP | 0607831 A3 | 11/1995 |

(Continued)

*Primary Examiner* — Kristy A Haupt
(74) *Attorney, Agent, or Firm* — Goodhue, Coleman & Owens, P.C.

(57) ABSTRACT

A smart storage system, method, and apparatus. One aspect provides a method for moving modular shelving units. A first tiered unit is determined to be accessed in response to input received. The first tiered unit within a modular shelving system is moved to an access location utilizing a motor. The first tiered unit is released for access by the user.

20 Claims, 17 Drawing Sheets

(56) References Cited

U.S. PATENT DOCUMENTS

| | | |
|---|---|---|
| 6,065,821 A | 5/2000 | Anderson et al. |
| 6,158,601 A | 12/2000 | Baker et al. |
| 6,167,670 B1 | 1/2001 | Reite et al. |
| 6,196,400 B1 | 3/2001 | Alneng |
| 6,216,993 B1 | 4/2001 | Morris |
| 6,536,614 B2 | 3/2003 | Hsia et al. |
| 6,634,511 B2 | 10/2003 | Manghera |
| 6,779,634 B1 | 8/2004 | Slagle |
| 6,880,297 B2 | 4/2005 | Johnston |
| 7,044,348 B2 | 5/2006 | McKenzie et al. |
| 7,077,068 B1 | 7/2006 | Agee |
| 7,497,531 B2 | 3/2009 | Gross |
| 7,511,626 B2 | 3/2009 | Siegmann et al. |
| 7,743,930 B2 | 6/2010 | Krohn |
| 8,117,972 B2 | 2/2012 | Winget et al. |
| 8,191,906 B2 | 6/2012 | Jensen |
| 8,297,726 B2 | 10/2012 | Ramm et al. |
| 8,388,073 B2 | 3/2013 | Richter |
| 8,414,093 B2 | 4/2013 | Moran |
| 8,424,983 B1 | 4/2013 | Strauss et al. |
| 8,442,676 B2 | 5/2013 | Kobayashi et al. |
| 8,588,966 B2 | 11/2013 | Michael |
| 8,700,211 B2 | 4/2014 | Shoenfeld |
| 8,733,860 B1 | 5/2014 | Burke et al. |
| 8,770,479 B1 | 7/2014 | Shoenfeld |
| 8,812,148 B2 | 8/2014 | Kharkover et al. |
| 8,882,433 B2 | 11/2014 | Bonora et al. |
| 8,919,578 B2 | 12/2014 | Villalobos |
| 8,955,648 B1 | 2/2015 | Weller |
| 8,977,383 B2 | 3/2015 | Kharkover et al. |
| 9,022,236 B1 | 5/2015 | Amendolea et al. |
| 9,245,405 B2 | 1/2016 | Michael |
| 9,255,729 B2 | 2/2016 | Rindlisbach et al. |
| 9,282,816 B2 | 3/2016 | Ahart |
| 9,326,599 B1 | 5/2016 | Sowers |
| 9,420,881 B2 | 8/2016 | Reid et al. |
| 9,456,688 B2 | 10/2016 | Moyer |
| 9,504,344 B2 | 11/2016 | Widner |
| 9,528,753 B1 | 12/2016 | Conner |
| 9,536,055 B2 | 1/2017 | Michael |
| 9,661,920 B2 | 5/2017 | Ahart |
| 10,010,170 B2 | 7/2018 | Ryner et al. |
| 10,102,855 B1* | 10/2018 | Sindhwani ............ G10L 15/22 |
| 2002/0011489 A1 | 1/2002 | Csiszar |
| 2002/0079313 A1 | 6/2002 | Grayson |
| 2003/0034167 A1* | 2/2003 | DeLand ................ H02G 3/288 |
| | | 174/50 |
| 2003/0155318 A1 | 8/2003 | Jacobs et al. |
| 2003/0159378 A1 | 8/2003 | Johnston |
| 2004/0238467 A1 | 12/2004 | Tully |
| 2005/0132924 A1 | 6/2005 | Bothun et al. |
| 2005/0236340 A1 | 10/2005 | Bothum et al. |
| 2007/0043600 A1* | 2/2007 | Solomon ............ A47B 63/067 |
| | | 705/28 |
| 2007/0095773 A1 | 5/2007 | Schwerman |
| 2008/0224579 A1 | 9/2008 | Juten |
| 2009/0302725 A1 | 12/2009 | Rogers et al. |
| 2010/0060121 A1 | 3/2010 | Helgesen et al. |
| 2011/0240493 A1 | 10/2011 | Adams et al. |
| 2011/0279951 A1 | 11/2011 | Kinsley et al. |
| 2011/0320035 A1 | 12/2011 | Kharkover et al. |
| 2013/0170129 A1 | 7/2013 | Sullivan |
| 2014/0193225 A1 | 7/2014 | Kharkover et al. |
| 2015/0053635 A1 | 2/2015 | Ahart |
| 2015/0175354 A1 | 6/2015 | Kharkover |
| 2015/0239658 A1 | 8/2015 | Christensen et al. |
| 2016/0066732 A1* | 3/2016 | Sarvestani ......... A47G 29/1201 |
| | | 232/24 |
| 2016/0166059 A1 | 6/2016 | Zohar et al. |
| 2016/0235195 A1 | 8/2016 | Ahart |
| 2016/0286956 A1 | 10/2016 | Guizzardi |
| 2017/0029198 A1 | 2/2017 | Pratt et al. |
| 2017/0055700 A1 | 3/2017 | Chung et al. |
| 2017/0096829 A1 | 4/2017 | Kharkover |
| 2017/0127825 A1 | 5/2017 | Melnick |
| 2017/0238701 A1 | 8/2017 | Ryner et al. |
| 2017/0299387 A1 | 10/2017 | Bryan et al. |
| 2018/0014641 A1 | 1/2018 | Pollard |

FOREIGN PATENT DOCUMENTS

| | | |
|---|---|---|
| EP | 1364595 A1 | 11/2003 |
| EP | 2386494 A1 | 11/2011 |
| GB | 2422774 B | 4/2007 |

* cited by examiner

MOTORIZED MODULAR SMART SHELVING AND STORAGE UNIT

PRIORITY STATEMENT

This application claims priority to U.S. Provisional Patent Application 62/569,335, filed on Oct. 6, 2017, and entitled Motorized Modular Smart Shelving and Storage Unit, hereby incorporated by reference in its entirety.

FIELD OF THE INVENTION

The illustrated aspects relate to smart storage. More specifically, but not exclusively, the illustrative aspects relate to a system, method for motorized, modular, smart cabinets, smart shelving, and smart storage units.

BACKGROUND

Technology advances have increased exponentially, and some portions of daily life have not kept pace or adopted the advances. For example, cabinets, shelving, drawers and other storage compartments/components lack options and features for real-time customization. What is needed than is a system, method for motorized, modular, smart cabinets, smart shelving, and smart storage units.

SUMMARY

Therefore, it is a primary object, feature, or advantage of the present invention to improve over the state of the art.

It is a further object, feature, or advantage to provide a motorized, customizable, Internet of Things (IOT) and sensor enabled modular storage unit for use in various storage implementations.

It is a still further object, feature, or advantage to provide a motorized unit that can be optionally customized with various pre-configured modular storage elements and motorized lift configurations depending on the available storage space and based on the storage space configuration.

Another object, feature, or advantage is to provide a smart storage system that has reconfigurable tiered shelving.

Yet another object, feature, or advantage is to provide a modular shelving system having tiered shelving actuated to different positions relative to a user access point for accessing any one of the tiered shelving using a motor and controller.

In one aspect, a smart storage system, method, and apparatus is disclosed. One aspect provides a method for accessing enclosed modular tiered units. The method includes providing an enclosed storage unit having a plurality of modular tiers within the storage unit accessible through an access point bay, access opening, opening or other point of retrieval 130 an actuator operably connected to the plurality of modular tiers, and an actuator controller operably connected to the actuator wherein the actuator controller has one or more pre-programmed, user activated and deactivated start and stop positions associated with each of the plurality of modular tiers. User input is received at the actuator controller for the one or more pre-programmed, user activated and deactivated start and stop positions and a tier is selected from the plurality of modular tiers to be accessed in response to the user input. The selected tier is actuated by the actuator from a raised or lowered position to the access point bay in response to a control signal from the actuator controller.

In another aspect, a smart storage system is disclosed. The smart storage system includes a fixed tier framework configured for storage and a plurality of modular units operably attached to the fixed tier framework in a user-controlled configuration. The plurality of modular units are interchangeable. A motor is operably attached to the fixed tier framework and a controller is operably attached to the motor. A user interface of the controller receives user input to control a position of the plurality of modular units for access by a user.

In yet another aspect, a modular shelving system is disclosed. The modular shelving system includes a structural framework and a plurality of tiered shelving units housed within and operably attached for movement in at least two opposing directions relative to the structural framework. An actuator is operably attached to the plurality of tiered shelving units. The motor moves the plurality of tiered shelving units in the at least two opposing directions relative to the framework. In one aspect, the system includes an electronic controller operably connected to the actuator and an electronic controller interface having one or more controls is for activating the actuator in the at least two opposing directions for controlling a position of the plurality of tiered shelving units relative to the framework.

One or more of these and/or other objects, features, or advantages will become apparent from the specification and claims that follow. No single aspect need provide each and every object, feature, or advantage. Different aspects may have different objects, features, or advantages. Therefore, the disclosure is not to be limited to or by any objects, features, or advantages stated herein.

BRIEF DESCRIPTION OF THE DRAWINGS

Illustrated aspects are described in detail below with reference to the attached drawing figures, which are incorporated by reference herein, and where.

DETAILED DESCRIPTION OF THE DISCLOSURE

Figure 1:
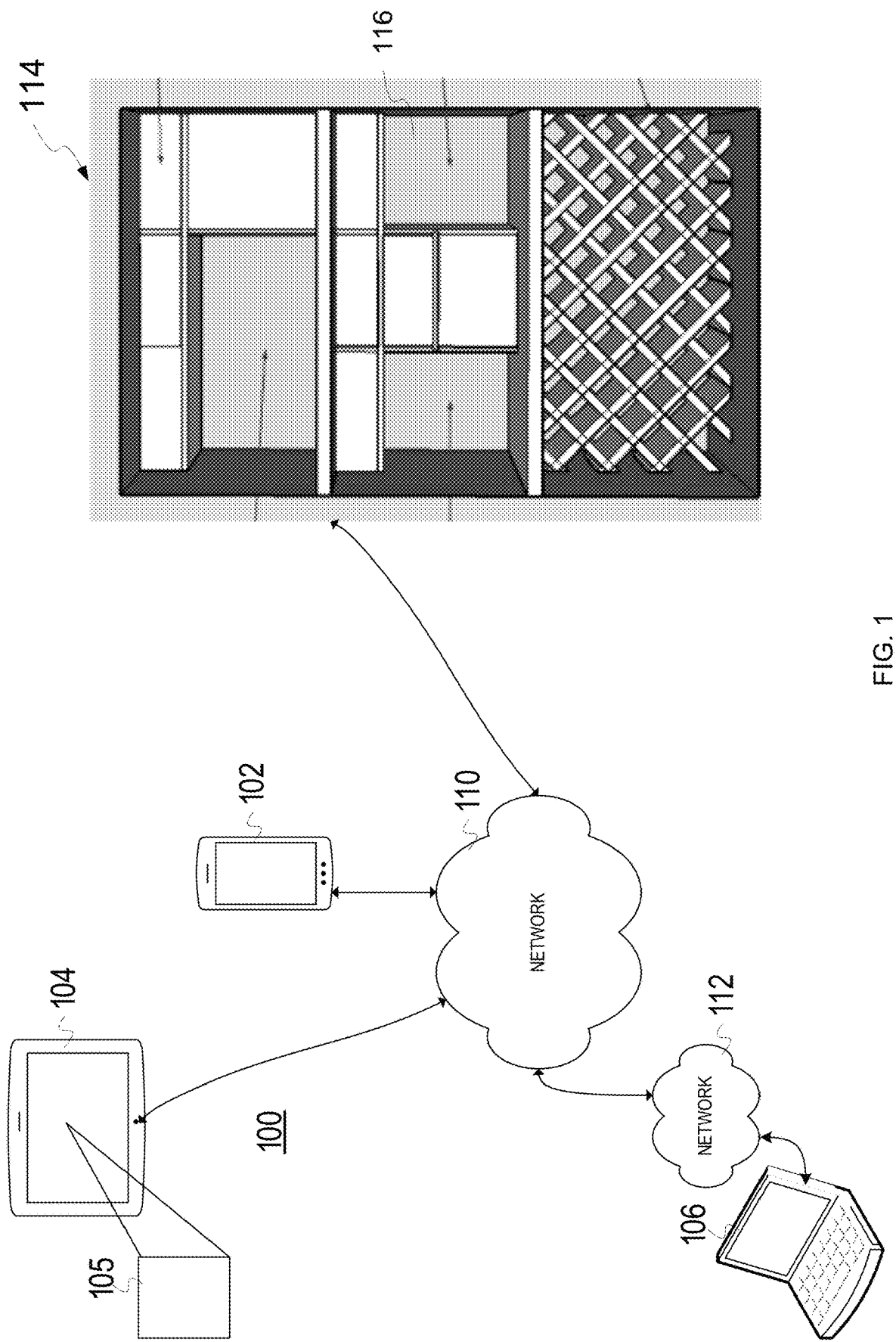
FIG. 1 is a pictorial representation of smart storage environment in accordance with an illustrative aspect.
Figure 2:
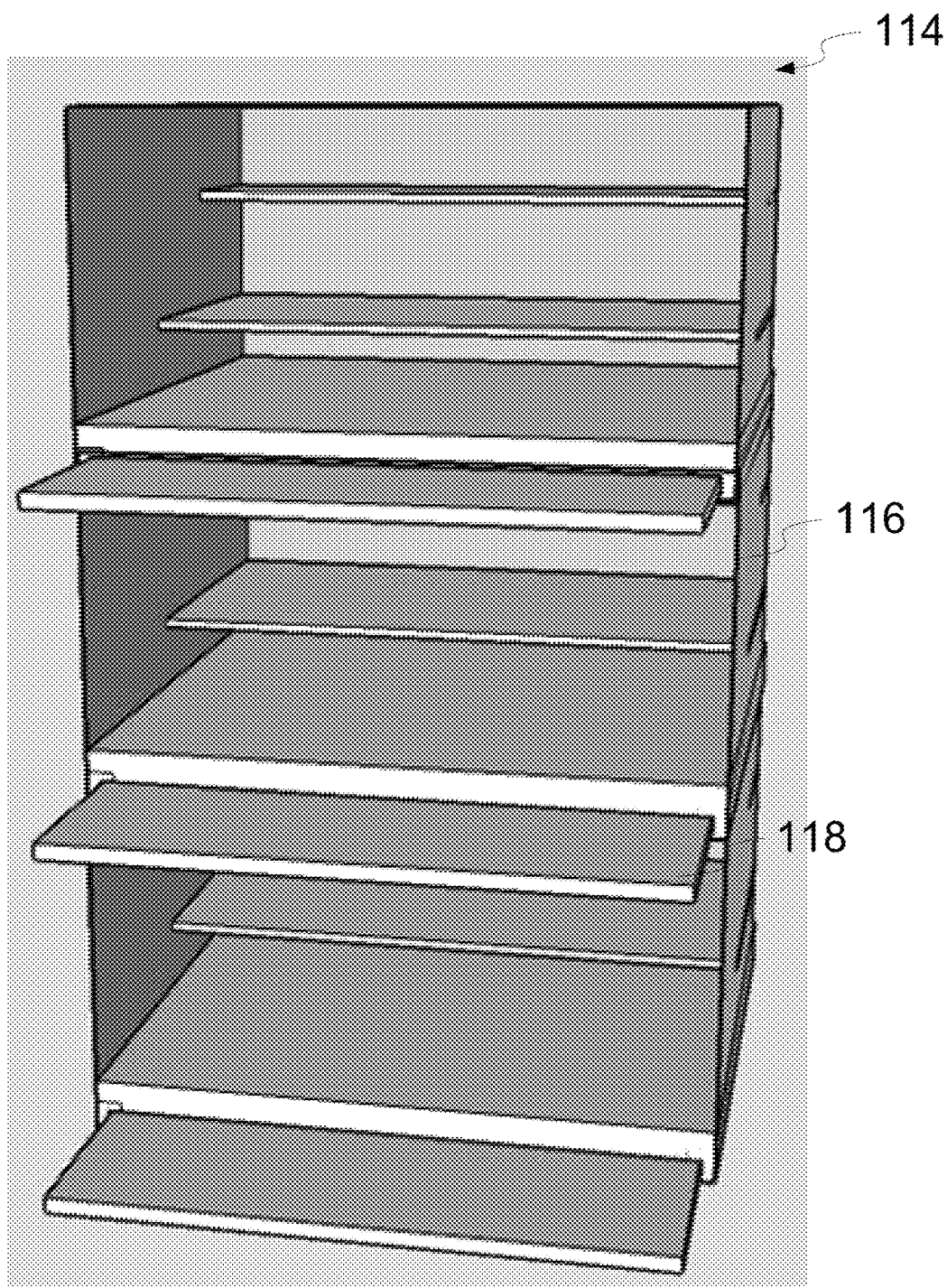
FIG. 2 is a pictorial representation of a smart shelving system in accordance with an illustrative aspect.
Figure 3:
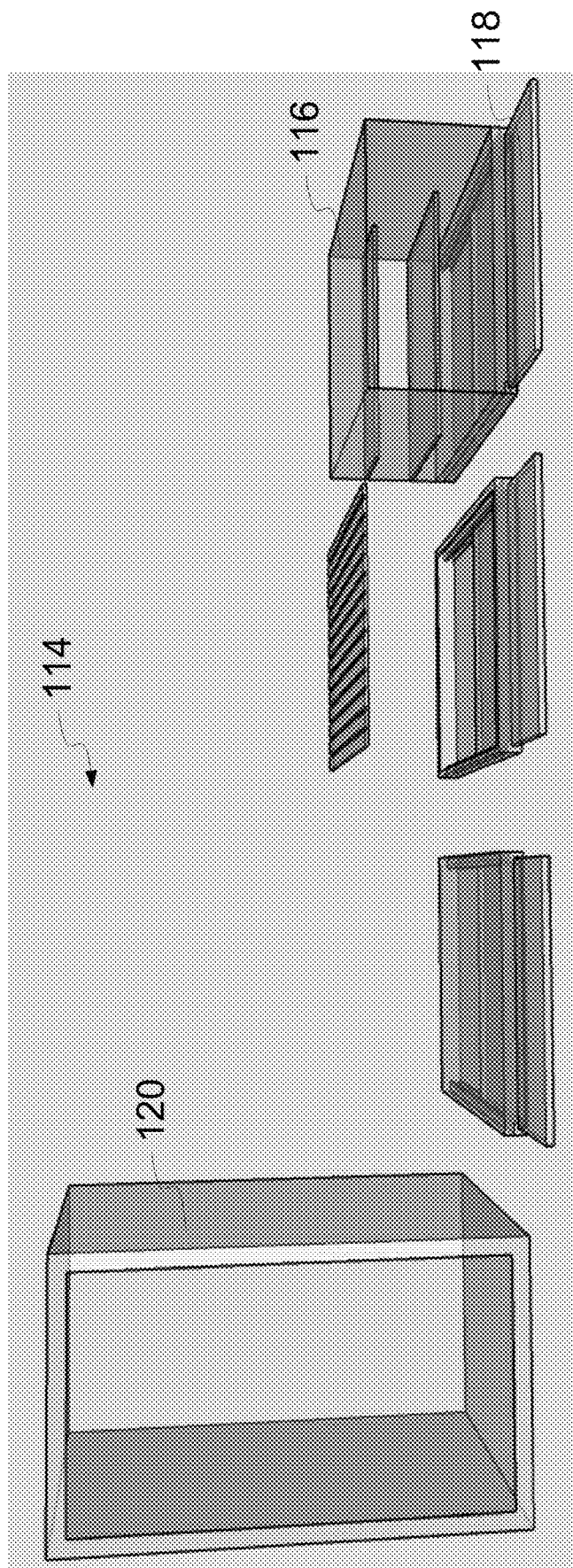
FIG. 3 is a pictorial representation of portions of the smart shelving system in accordance with an illustrative aspect.
Figure 4:
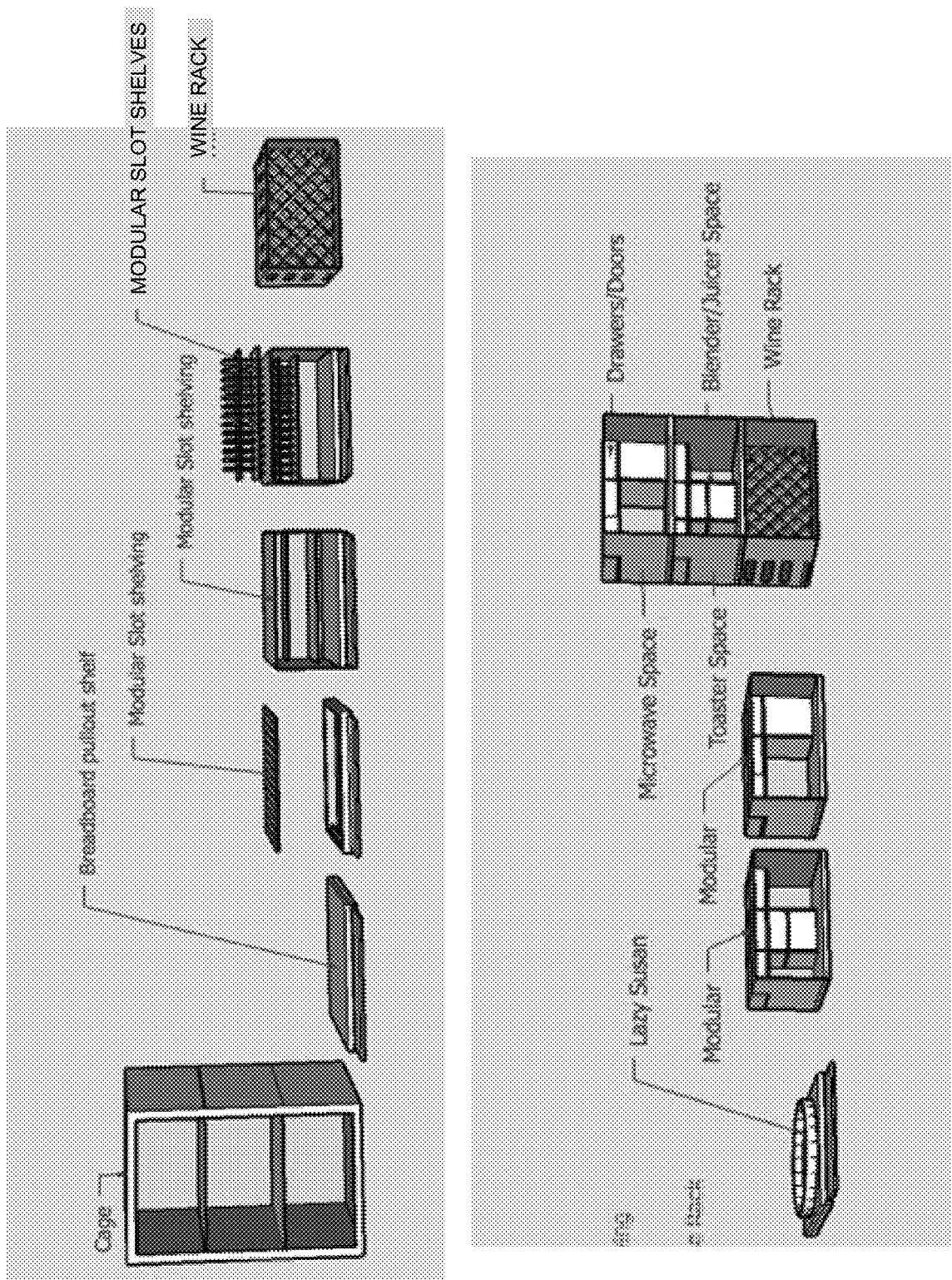
FIG. 4 is a pictorial representation of portions of the smart shelving system in accordance with an illustrative aspect.
Figure 5:
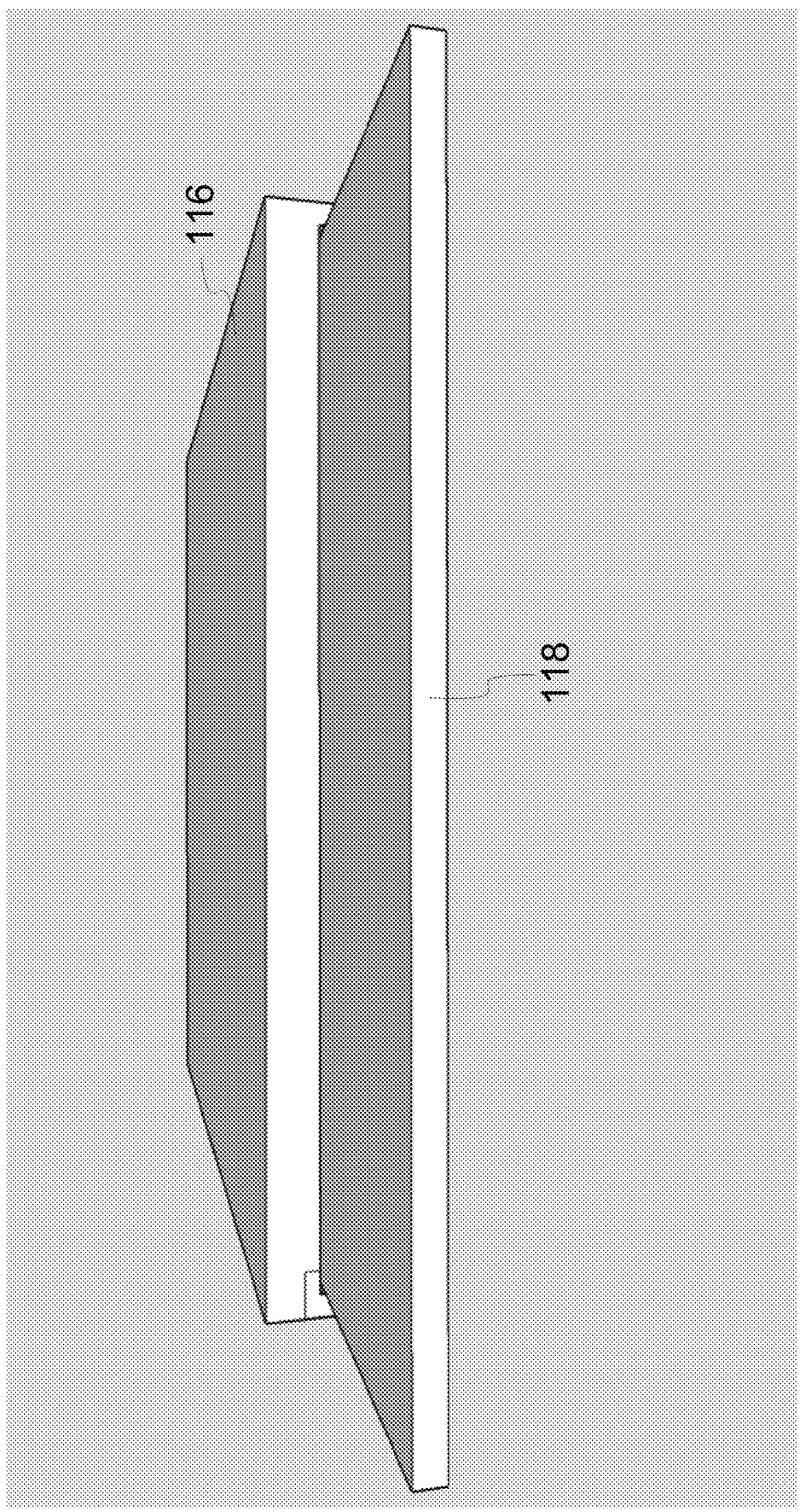
FIG. 5 is a pictorial representation of a smart shelf in accordance with an illustrative aspect.
Figure 6:
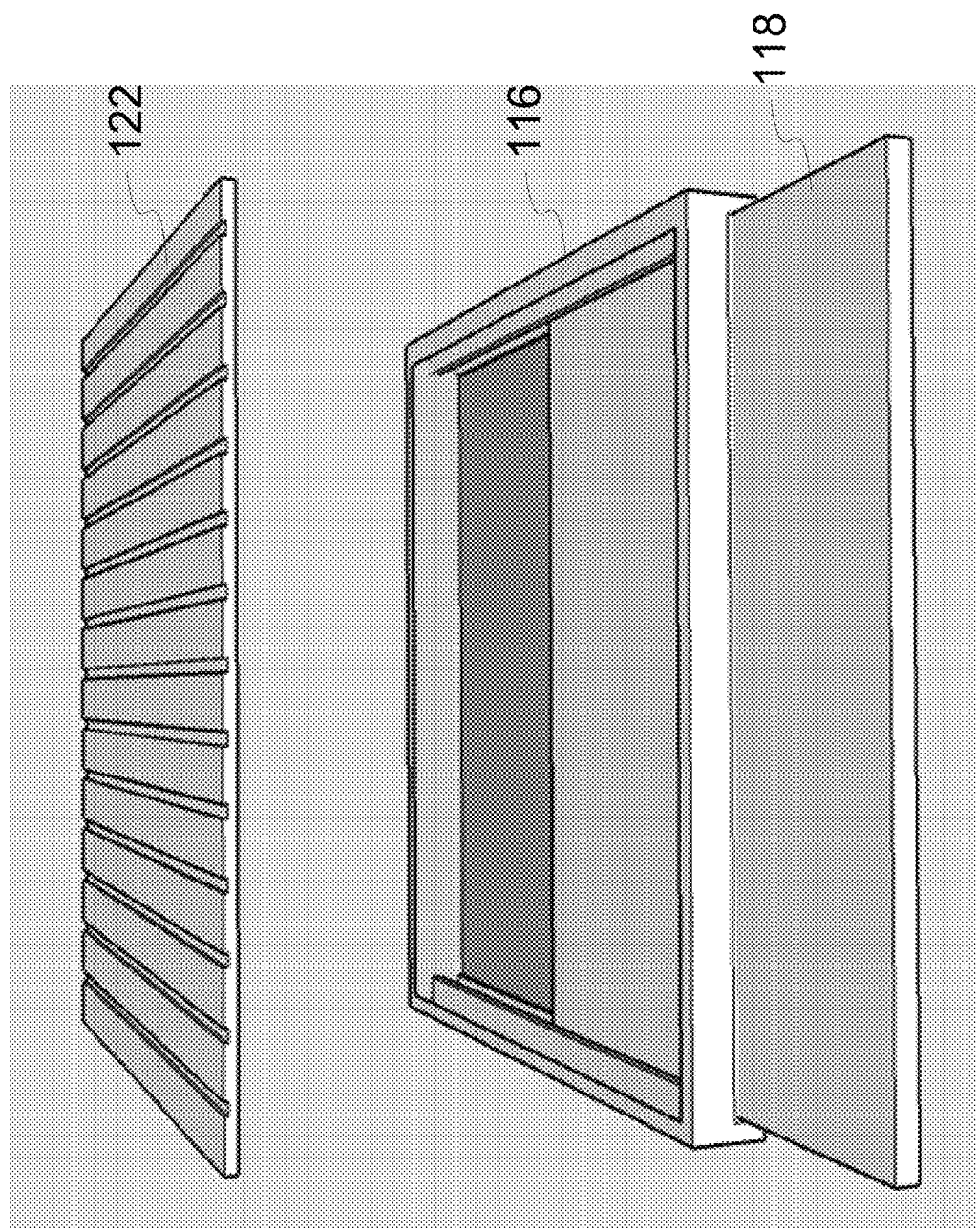
FIG. 6 is a pictorial representation of another smart shelf in accordance with an illustrative aspect.
Figure 7:
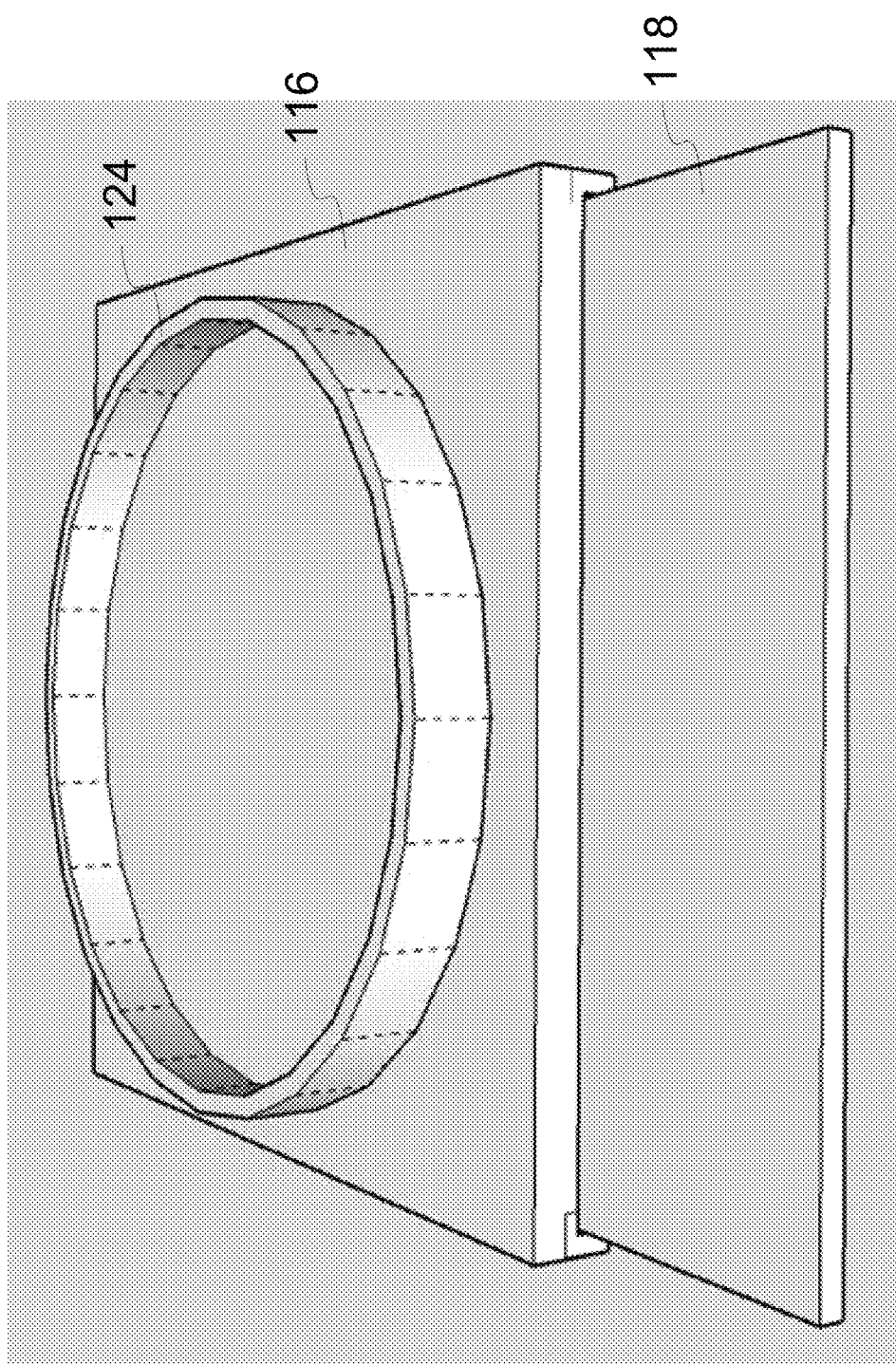
FIG. 7 is a pictorial representation of another smart shelf in accordance with an illustrative aspect.
Figure 8:
FIG. 8 is a pictorial representation of a structural framework in accordance with an illustrative aspect.
Figure 9:
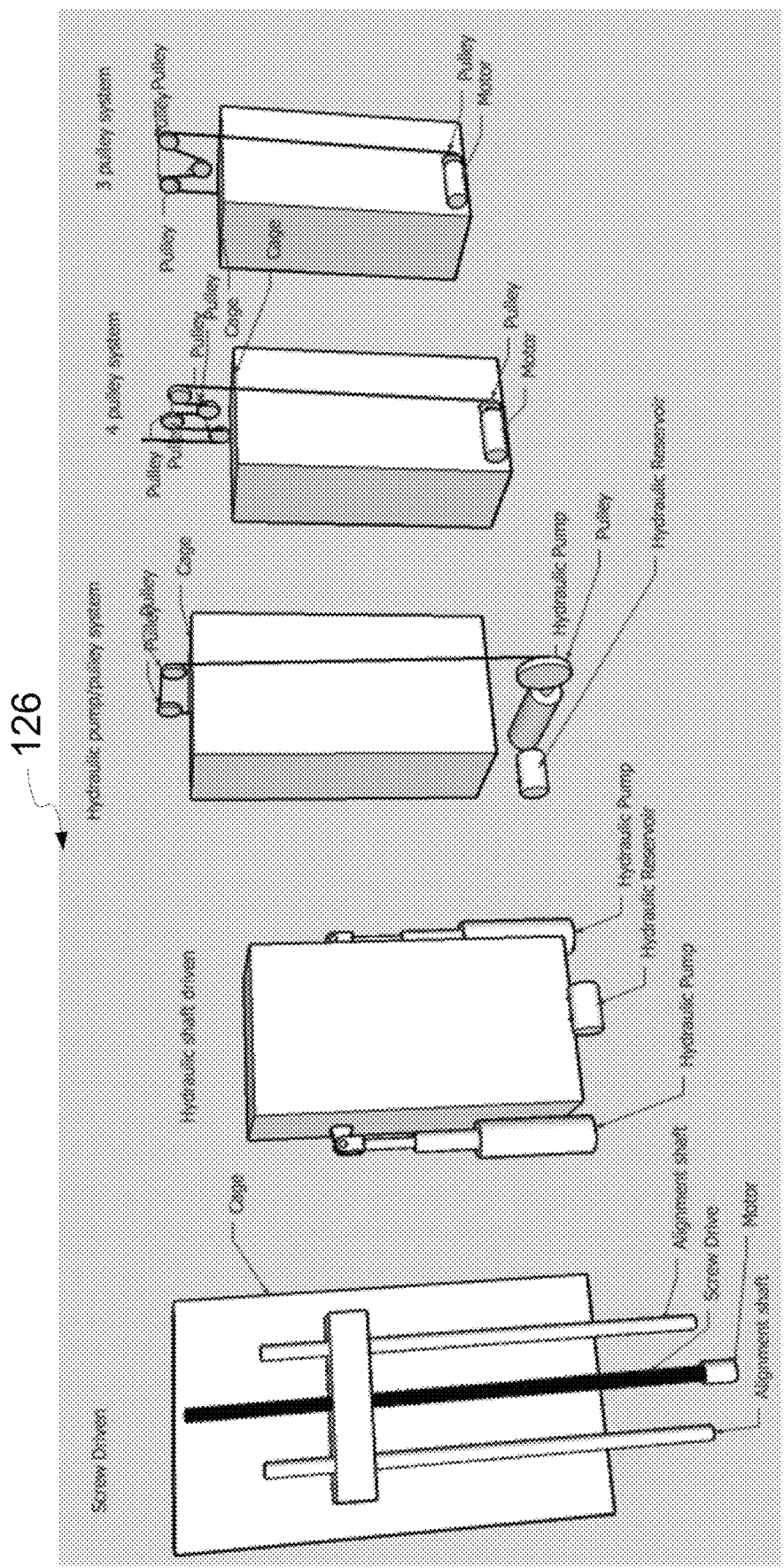
FIG. 9 is a pictorial representation of drive mechanisms of a smart storage system in accordance with an illustrative aspect.
Figure 10:
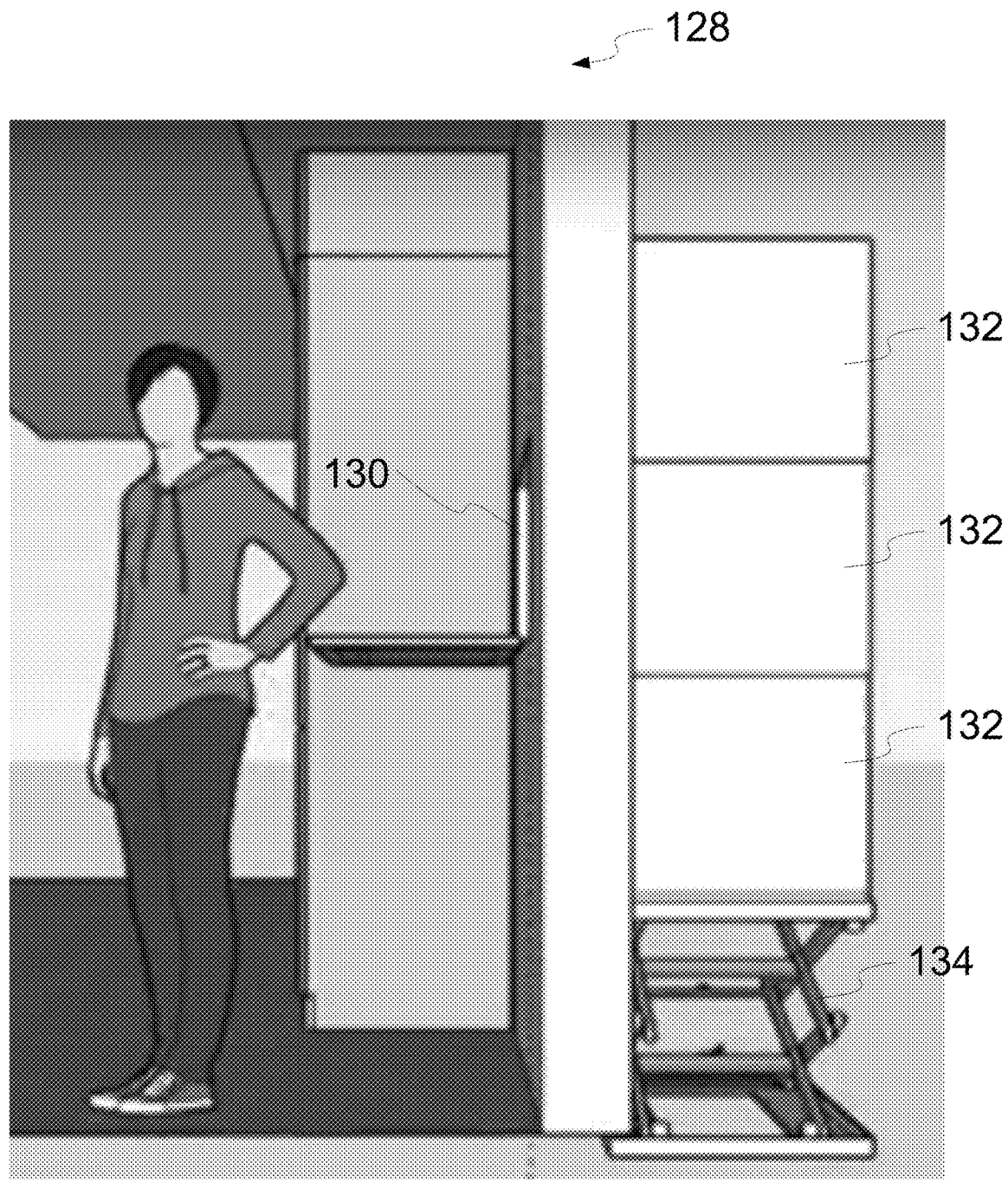
FIG. 10 is a pictorial representation of drive mechanisms of a smart storage system in accordance with another illustrative aspect
Figure 11:
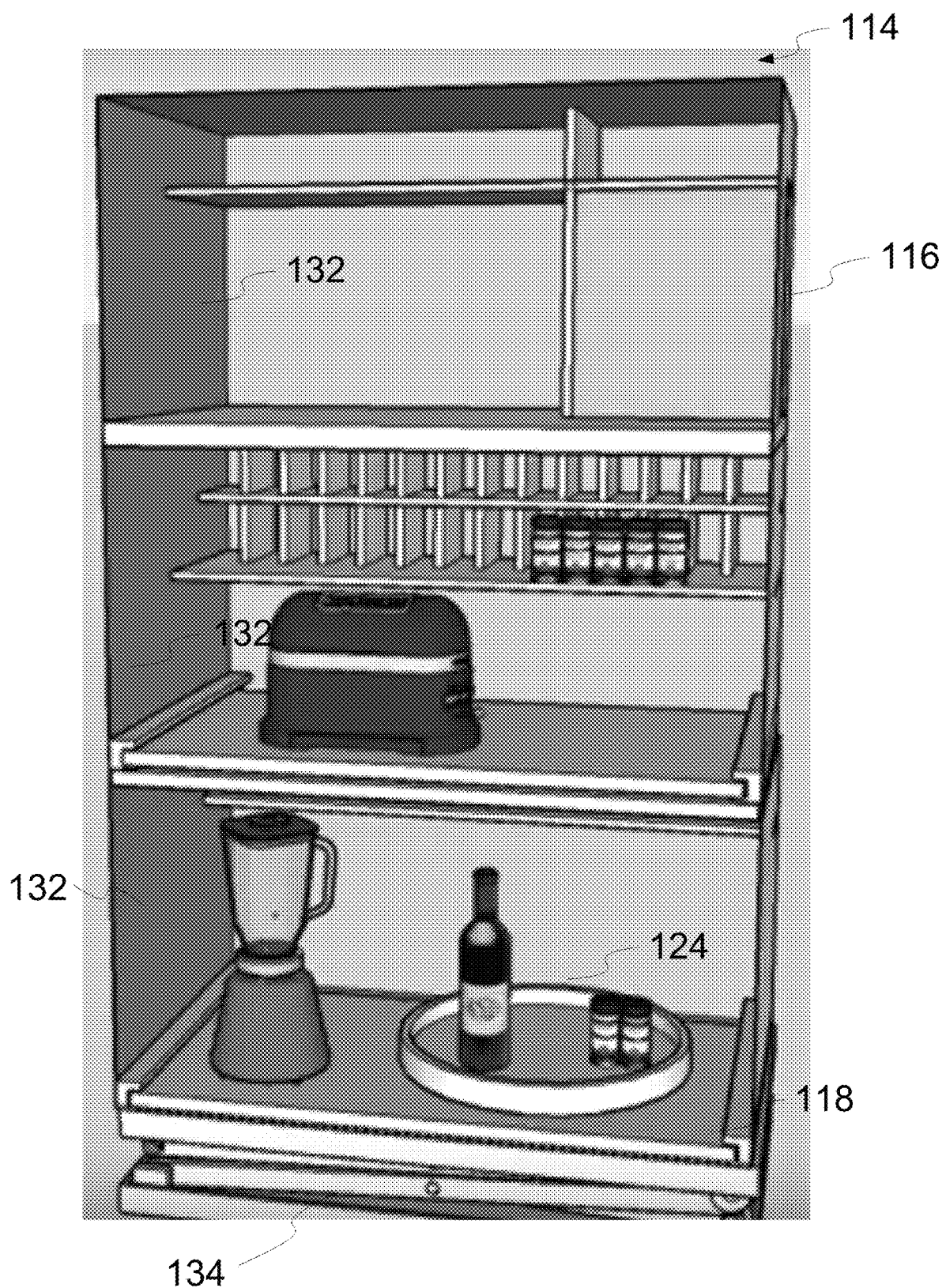
FIG. 11 is a pictorial representation of a smart shelf and storage system in accordance with an illustrative aspect.
Figure 12:
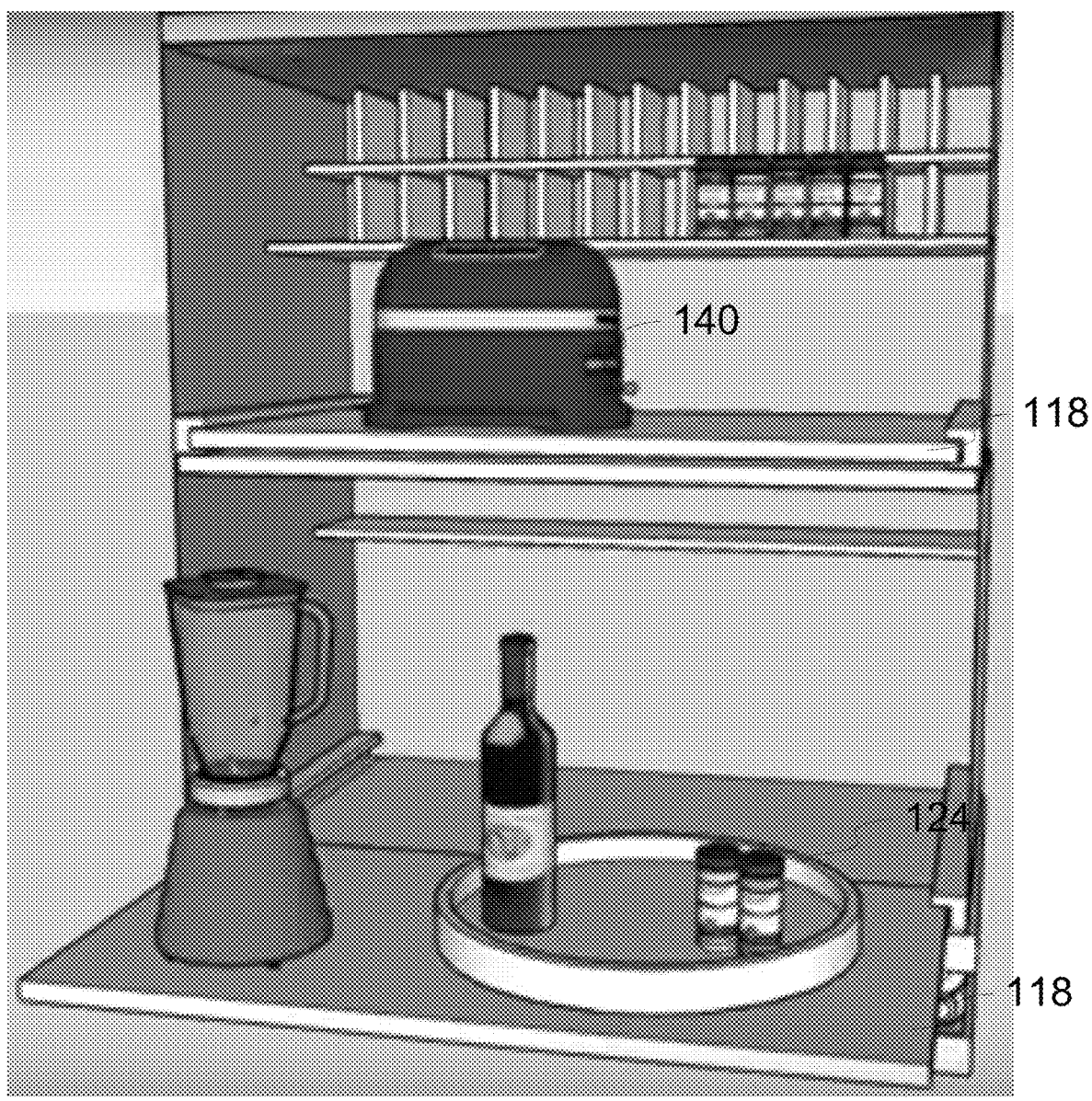
FIG. 12 is another pictorial representation of the system shown in FIG. 11.
Figure 13:
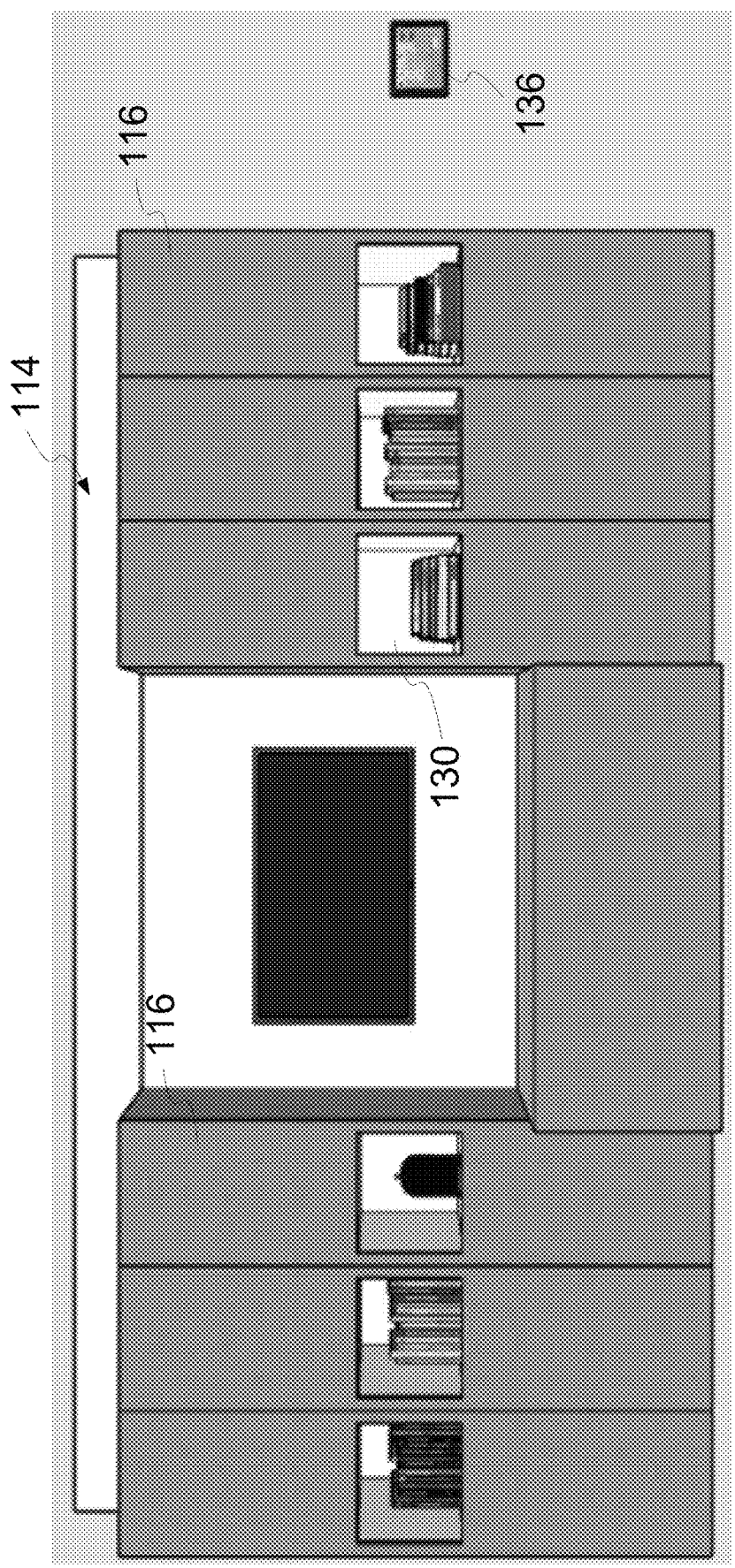
FIG. 13 a pictorial representation of a smart shelf and storage system in accordance with another illustrative aspect.
Figure 14:
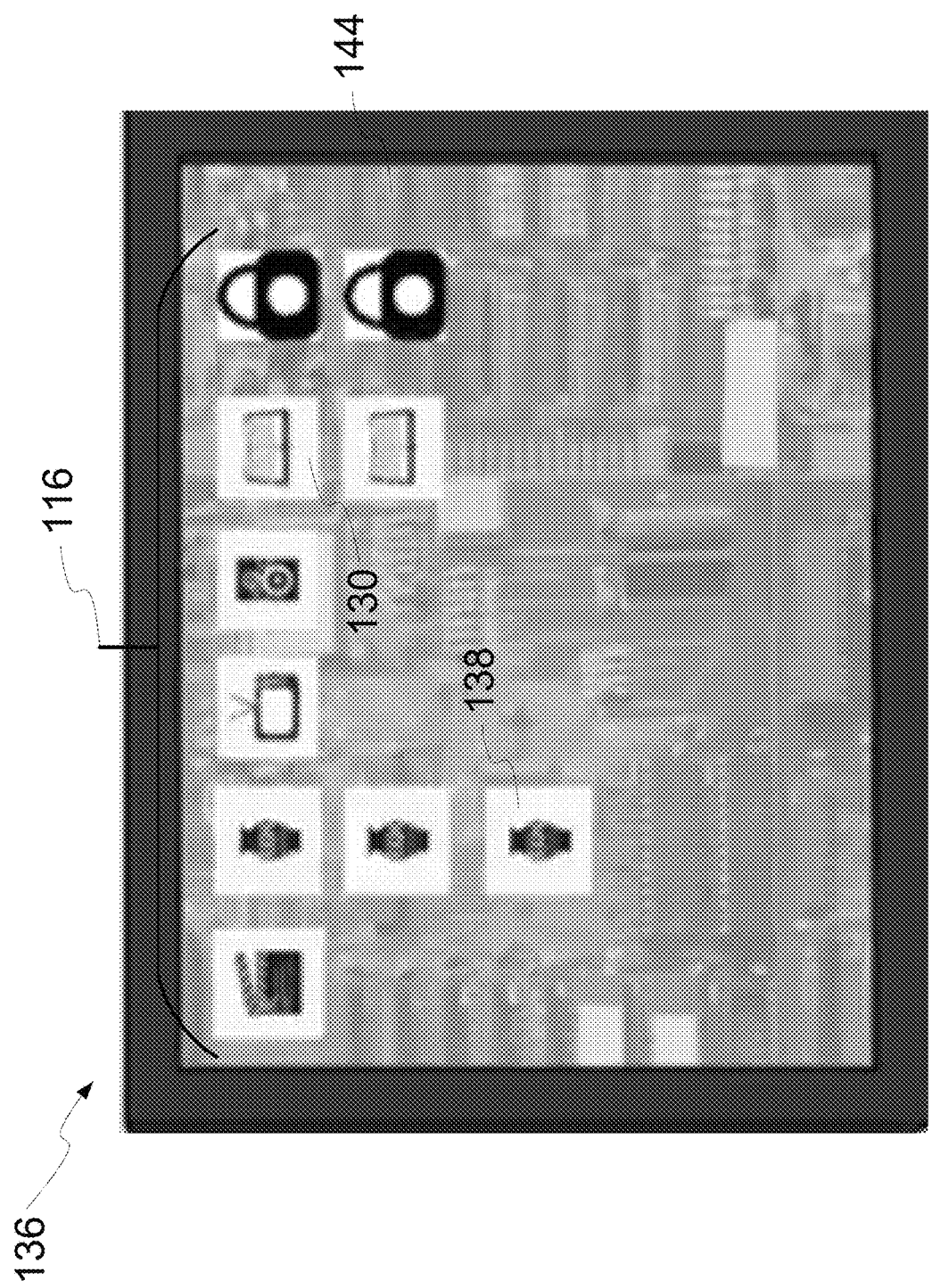
FIG. 14 is pictorial representation of a controller for a smart shelf and storage system in accordance with an illustrative aspect.
Figure 15:
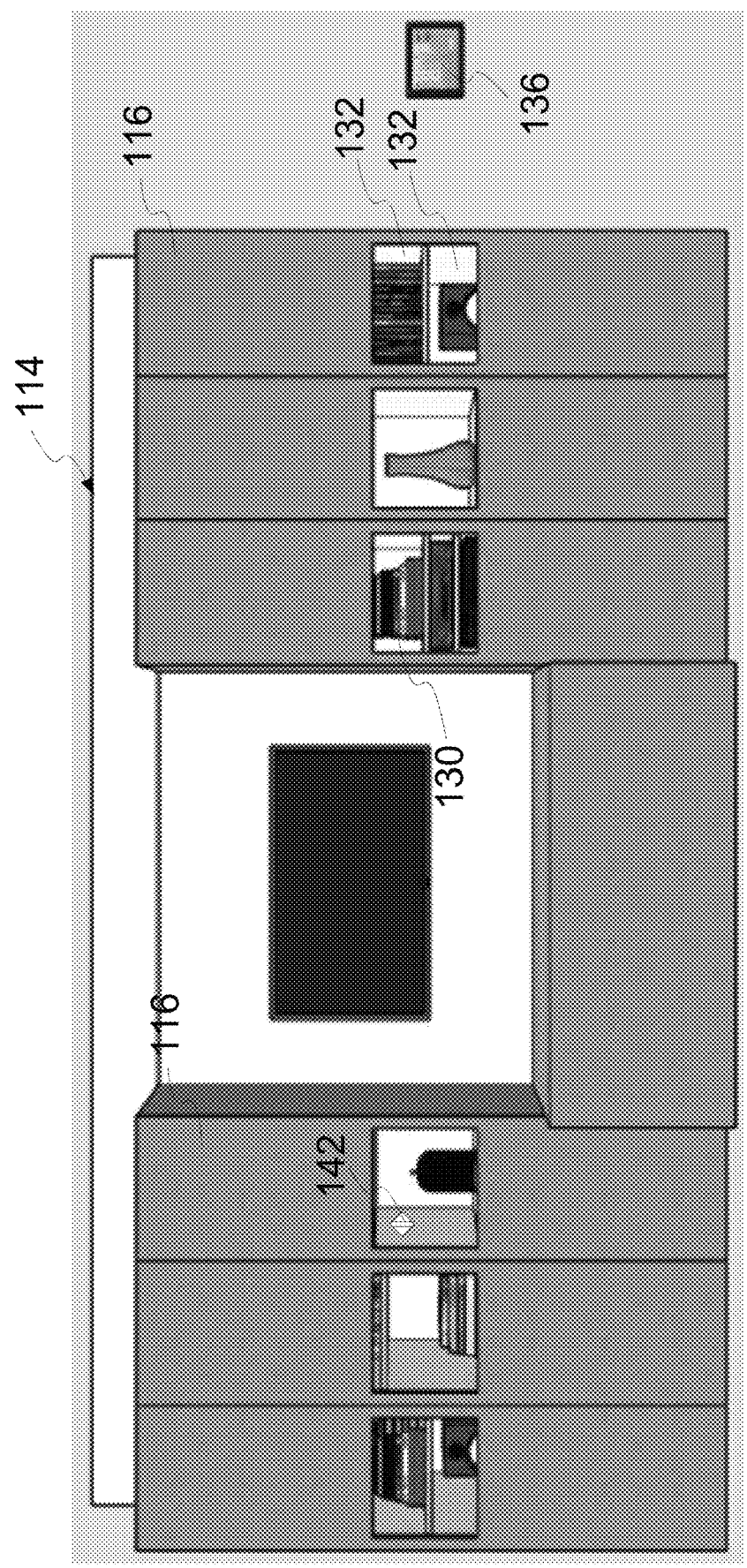
FIG. 15 is a pictorial representation of the system shown in FIG. 13

The illustrative aspects shown pictorially in FIGS. 1-17 provide a system and method for smart storage systems and units. The storage systems and units may include or be integrated in shelves, drawers, cabinets, pantries, closets, jewelry holders, accessories, furniture, and so forth. The smart storage systems may also be referred to as smart shelving systems, modular storage systems, or so forth. In one aspect, the smart storage system may include a structural support. The structural support provides the load bearing components of the smart storage system.

In one aspect, the structural support may include any number of guides for moving tiered/modular units within the smart storage system. For example, any number of rails, guides, tracks, or so forth may be utilized to both install, move, and remove the modular units. The structural support may also be configured to provide power for one or more drive mechanisms of the smart storage system. For example, the smart storage system may be powered through a standard 110 V electrical interface. In other examples, the smart storage system may be powered utilizing batteries, fuel cells, solar cells, or so forth.

The tiered units 132 may be moved both vertically and horizontally within the smart storage system. In one aspect, a selected tiered unit may be moved to an access position for utilization by a user. Movement of the tiered units may allow common dead space within storage to be more fully utilized. As is described herein, any number of modular units may be utilized or swapped out based on the needs of the user. For example, the tiered units may include a workspace for a user, such as a cutting board, knives storage, and electrical outlets. For example, modular drawers, shelving, and work spaces may be removed from and inserted into the smart storage system.

The smart storage system 114 may utilize a user interface and/or (motor, actuator) controller 136 (e.g., touch screen, microphones, buttons, switches, etc.) to control the motion and operation of the smart storage system. In one aspect, the user may control the smart storage system utilizing voice controls, such as "retrieve my jewelry passcode 3948." The jewelry shelf may be moved into position once the passcode is authenticated (e.g., voice identification, correct passcode/password/command, etc.). In one aspect, the smart storage system may be utilized for commercial spaces that require different goods be accessible at different times of the day, such as businesses, restaurants, hospitals/care facilities, and so forth. Different sets of tiered units may be moved into position based on user preferences 138, parameters, or settings, such as time of day, day, calendar entries, pre-authorizations, user, mode of operation, date, and any number of other factors.

The illustrative aspects provide unique ways of utilizing available space in a safe and secure manner. Dead space is minimized while user satisfaction with the smart storage system is maximized because of interchangeability, access, security, smart management, and so forth.

Motorized Tiered Modular SMART Shelving and Storage Unit

A motorized tiered shelving assembly 116 that pairs fixed tier and modular shelving configurations combined with customizable access points and customizable motor start and stop points. Additional sensor and network based elements are tied into the storage unit. The tiered assembly utilizes motorized lifting and lowering to provide motorized access to each storage tier at the access point level.

Main Access Tiers

The three main motorized caged tiers are fixed and the tier size configuration is determined based on the travel space requirement needed to access each tier inside of the access tier compartment. Each fixed tier compartment can also be customized to accommodate Lazy Susan or Turn Table 124 functionality in the center or a customized location at any tier. Additional fixed tiers and their starting and stopping points can also be customized by adding or removing additional fixed tiers at the optional fixed tier locations that create the added start and stop points.

Modular Tier Configurations

Modular shelving configurations are used to add or enhance additional storage space or add new storage elements around stored items. Each fixed tier is modularly designed to add pre-configured shelving elements that take advantage of negative space around stored items. A key component of the invention is the transformation of negative storage space into maximized space, which is accomplished through the tiered and customizable modular shelving designs used in the fixed shelving tiers within various modular configurations.

Negative storage space is storage with limited access or space that is less accessible or unusable due to its location; negative space also encompasses unused space around stored items in a storage space. A key element of this invention is the ability to modularly configure and customize negative space into easily accessible storage space through the process detailed in the invention.

Fixed Tier Configuration

Each of the three main fixed shelving tier's height and width is predetermined and configured based on the setup and required travel space in the storage location. The access tier is also configured based on the design and configuration of the storage location. Depending on tier size of the fixed tiers; each fixed tier level is pre-configured to accommodate 1-4 additional optional fixed tier levels within the same fixed tier level. When an additional tier is added to the preconfigured tier slot, an additional tier level and start and stop point is created at each level.

The fixed tiers have a lift off shelf top 122 that uncovers additional storage space under each fixed tier level. The fixed tiers can also be configured to manually or mechanically pull in an out from their access tier location for greater access to stored items. The fixed tiers can also hide smaller additional pull out shelving trays or items like a pull-out bread board. The storage space inside the fixed shelving also provide additional storage space and can also store the various modular shelving configurations when not in use. The lift off countertop has two sides; one that is a fixed wood, plastic or other material with a flat non-slotted pattern and the opposite side having slots that allow for the customizable modular shelving panels or turn-table or Lazy Susan capabilities to be inserted into the base of the shelves or into the pre-cut modular shelving slots.

Another key component of the invention is each fixed tier level is designed to be modularly customizable through shelving slots that allow for the utilization of various pre-designed modular shelving configurations that fit into the slotted section of the base, tops and sides of the shelves. The slotted configurations are cut into the shelving panels at every 2 inches at the base and the bottom of each fixed tier with additional horizontal slots every 2 inches at the interior sides of the cabinet. The 2-inch spacing of the slotted section inside the cabinet allows for fully customizable modular configurations based on the desired set up of each shelving tier. The modular units and shelving configurations utilize a locking pin mechanism to secure the modular configurations in place.

Fixed Tier Level Additions

Each shelving tier can also be customized with additional fixed tier levels that create a new access tier start and stop point by adding additional fixed shelving tiers at any desired level. The fixed tiers can be added or removed by inserting or removing the quick release auto-lock safety pull pins in the front corners of the shelving structure. These safety pins hold the fixed shelving in place and can be used to add anew fixed shelving tier in the desired numbered shelving location by locking the rear portion of the shelf in place in the with the slotted side and rear slotted configuration and then locked in place with the quick release auto-lock safety pull pins in the correct shelving number position.

Stop point are pre-programmed into a module and activated via insertion of additional fixed tiers at the optional fixed tier levels. When a new optional fixed tier is added at the chosen shelving level, the subsequent number position and start and stop point is indicated at the system level related to the shelving position number and adds an additional start and stop point in the raising and lowering process.

As additional fixed tiers are added or removed the total number of access tier stop points are modified as the new shelf tiers and numbers are reassigned on the control unit and the motor control device which controls the motor stop and start points. The system utilizes a tiered number system and push pull pin to indicate an additional tier has been added.

Motorized and Servo Driven Feature Options

Optional Access Tier Cover

Prior to the mechanized motor engaging a motorized cover lowers across the access tier to prevent injuries when in use.

Mechanized Smart Shelving Configuration

As an option the fixed tiers can be also configured with servos to mechanically pull the fixed shelf in and out via mechanized push pull shelving design which allows for motorized fixed tier access at each tier of the storage unit when in the access position.

The tiers can also be customized in locations that can accommodate side to side mechanized access to the cabinet. The side by side access is configured with a conveyor configuration that gives access to stored items stored at either side of a tier access position and are moved into place via the conveyor.

Multi-Tiered Shelving Storage Workspace Table

In a configuration with limited access space or no room for additional counter space a secondary hidden work table 118 is placed in a wall mounted configuration or attached to the shelving unit just below the access point. The work table can raise and lower manually or via mechanically servo and lift up and lock into place when in use and unlock and collapse against the lower level of the cabinet structure, enclosed framework, enclosure or structural framework 120. As an additional option the workspace table unit can also be motorized via servos or manually raise and lower the position of the workspace table to any desired level.

Motorized Lift Configurations (126)

Gear Driven Configuration

The gear driven system is used to fully maximize shelf space and can be contained in the top, bottom or rear portion of the shelving unit.

The motorized assembly is configured with a gear configuration to raise and lower the tiers via a track assembly that guides the tiered shelf assembly up and down to position each of the storage tiers in the access position of the cabinet.

Hydraulic Configuration

The hydraulic configuration is used to drive an inter-concentric gear maximize space and lift capacity. The lift is configured at both sides of the tiered unit.

The motorized assembly is configured with a hydraulic configuration to raise and lower the tiers via hydraulic lift that guides the shelf assembly up and down to position each of the storage tiers in the access position of the cabinet.

Multi Configuration Motorized Chain Pulley and Track and Roller System

The motorized assembly can be contained in the lower or upper portion of the cabinet structure or on the roof of the structure or the building itself depending on configuration and to further maximize storage space based on the location of the storage cabinets. The motorized assembly can also be contained on the front, side or back of the structure.

The motorized assembly is configured with a chain pulley to raise and lower the cabinets on a track and roller system that guides the shelf assembly up and down to position each of the storage tiers in the access position for the cabinet.

The track and roller system is used to guide the shelving system up and down the cabinet structure. The track acts as a guide for the rollers. The track can also be implemented or retrofitted into existing cabinets in a number of configurations based on the location and desired access point for the cabinet structure.

Motorized Worm Drive Lift

A worm drive is configured in the rear, side or middle of the cabinet and raises and lowers the tiers intro place via a circular worm drive that turns forward or backwards to lifts the structure from a fixed position inside of the cabinet.

Motorized Scissor Lift Configuration (128)

A scissor lift configuration can also be utilized as the means to lift and lower the cabinet tiers. The scissor lift 134 can be installed in the top or bottom tier of the cabinet structure and is utilized in instances where the upper or lower tier of the storage configuration is obscured or blocked. The scissor lift configuration maximizes the interior storage space of a cabinet tier and can offer greater access to typically obscured storage space.

Over and Under the Rainbow Configuration

Additional installation options or alternatives for track based roller system—concept around an over and under the rainbow storage configuration to maximize storage space at the top and bottom of the roller configuration Top and bottom tiers rotate in a fixed stable position around the U-shaped bracket and the upper and lower rainbow tiers do not connect to the fixed tiers but move independently around the fixed shelving tiers at the upper and lower tiers Power Options Internal Power Each shelving configuration is powered via preinstalled wiring that gives each tier access to fixed power outlets that are preconfigured for access to power.

Tiered Power Strips

Each shelving tier also can have its own electrical power strip to ensure an always ready power source for each electrical appliance or power tool contained in each shelving tier. Each power strip can be customized with any number of outlets and utilizes the same power source as the motor used to raise and lower the shelving tiers. The fixed power strip option at each tier allows the appliances to remain plugged in and stay in a fixed position.

Fixed Power Outlets

A second power option calls for the placement of fixed power outlets in the sides or back panels of the cabinet structure. Standard fixed wall outlets can also be used as a power access point.

IOT and Sensor Configurations

Remote Control and IOT Configuration

The lift motor can be controlled via a standard remote control or as a wall imbedded non-mobile control unit. The system can also be controlled via a known IOT frequency such as Infrared, Z-Wave, Zigbee, Bluetooth, RF, App or controlled via a mobile device.

Smart Cabinet Sensor Placements and Utilizations

In aspects without a mechanized safety cover over the access tier, safety sensors are placed on the inside of the cabinet access point that disengages the motor to help prevent injury and ensure safety if a hand or other body part crosses the safety sensor. The sensors can also disengage if a storage item is in the path of the safety sensor.

Access tier light and rear camera configuration is utilized to remotely connect via IOT to remotely control the lift capabilities and remotely view contents of the storage tiers. Sensor can also be used to control the stop and start points of both the fixed tier stop point and the customizable start and stops at the access tier.

Secondary sensors are placed in each tier that ensures the selected shelving tier can be fully customized with stops at the appropriate desired stop point. The sensor can be used to quickly access various levels of the shelving by simply selecting the number associated with the shelving unit that a user need to access.

Additional sensors are placed to indicate when the maximum capacity for a shelf is approaching and has been reached. A maximum load capacity alert is indicated at the system level. The overload safety system also come pre-equipped with a weight limit indicator that utilizes a spring and limit switch, which invokes as the unit approaches its weight limit, which activates the mechanism that disengages the motor.

Additional optional motion sensors are placed in the underside of the cabinet structure for rodent detection that indicates micro movements inside of the cabinets that can indicate the presence of rodents or pests.

Applications

What follows are exemplary applications, which are not exhaustive of those contemplated.

Kitchen or Bakery

The tiered shelving units can be used with specific tiers containing kitchen appliances such as a blender, mixer, microwave, toaster, coffee maker. The user simply selects the tier they wish to utilize and the selected tier is raised or lowered. The appliances can be pre-plugged in and ready to use or can be used by simply plugging them into the fixed power outlet. The shelving can also be used for standard kitchen storage such as glasses or pots and pans. The shelving can also be used as a secondary countertop with the top middle and lower storage levels all accessible from the access point at standard countertop level.

In Home Medicine Cabinet

The tiered shelving unit can be customized down to the size of a standard medicine cabinet or smaller and can give each user their own private tier in the medicine cabinet. Each tier can contain personal items such as toothbrush, medication and other personal items commonly stored in a medicine cabinet. The cabinet can also be made secure for medication reconciliation through a simple password or fingerprint identifier.

Shoe Rack

Tiered shelving unit utilizes a C configuration that allows access to each access tier level to for easy access to a specific pair of shoes. The access tier allows for access across a row of stored shoes.

Easy Access for People with Disabilities: Accommodations are made to the unit specifically at the access point to optimize the access point at the desired level or additionally the work space can raise or lower manually or via a servo to optimize the location of the workspace when in use.

Safe and Valuable Storage

Access point can be configured with a metal door or steel door with locking mechanism small configuration modifications are made that utilize secure tiered storage to hide a safe for valuables or a gun safe that is out of view when not in use. The tiers can also be disguised to make it difficult to recognize the additional access to hidden tiers. The tiers can be accessible though simple lock and key or through modern means such as a fingerprint, voice recognition, retina scan or other identity based security mechanism.

Features and Benefits

A key improvement of the invention is the tiered customizable modular configurations, which take advantage of negative or wasted space Wasted space is space lost because you don't typically fill a standard non-motorized appliance storage cabinet space to maximum capacity The system takes the wasted storage space typically found above and around items stored in a standard storage cabinet and trades that wasted space for the motorized convenience of tiered storage giving users the advantage of motorized, organized ready to use access to all items Reduction of Negative Space Storage: The invention has numerous utilizations in instances where access to specific areas of storage is blocked or storage access is limited. Examples include obscured floor or upper level storage areas that can become accessible through motorized storage implementations The inventions always on power capabilities offers the added advantage of having multiple pre-plugged in appliances ready to use at the push of a button A key improvement of the mechanized or manual hidden work table allows previously unused space to be modified into a useable readily accessible work space Full Sensor and IOT technology capabilities ensures user safety, lift start and stop mark reliability and full system modification programmability Aspects of the present disclosure include a method for moving modular tired units by determining pre-programmed, user activated and deactivated start and stop points that provide customized access to each tiered unit at the access point bay, by raising or lowering each modular tier to the access point and by determining a tiered unit to be accessed in response to input received. A control switch can be wired, programmed and connected for determining activation or deactivation of selectable pre-programmed start and stop locations for each tiered unit in response to the pre-programmed user selected input. Activating the drive motor and moving the selected tier to the activated stop location and past any deactivated stop locations operates the selected tier to a user access point. Each of the tiered access points can be equipped to provide power to appliances or accessories at each tiered unit. Each tiered unit can be used as modular storage or user work space that is designed and pre-configured to allow for customized modular tier configurations by adding or removing modular shelving or wall customizations that utilize pre-configured tier and shelving slot assemblies that are designed to fit within the customizable modular configurations. The modular shelving unit can be adapted by adding, removing, changing or reconfiguring the modular configuration and indicating at the system level that a new tier has been added or removed and creating or deleting a new start and stop point based on the tier numbering system at the control unit. The adding or removing of non-fixed modular tiers can be performed utilizing a quick release pin system and/or a dowel insert configuration for each added or removed non-fixed tiered unit. A motor can be controlled by a controller with a plurality of pre-programmed user selectable start and stop points to create customizable starting and stopping points for a variety of customizable tiered unit configurations. By mechanically or manually extending an additional inner shelf tier from a fixed tier or non-fixed tier extending horizontally provides additional shelf or workspace access for each tier in the access bay position. A lift motor that when activated, automatically can determine the access location stop point through the user activation or deactivation of one or more of the sensors that controls the pre-programmed stopping points of the smart storage system.

A smart storage system of the present disclosure provides another illustrative aspect. The smart storage system can include a fixed tier framework configured to receive a plurality of modular unit configurations, a motor can move a shelf or work station portion of the modular unit out for access by a user, and a controller controlling the motion of one or more of the servo-equipped modular units in response to input utilizing at least the motor and the plurality of modular units which are pre-configured and interchangeable within each modular tier. The controller can include a user interface for receiving input from the user at a fixed control unit, a remote controller or a mobile device. A power interface powering the motor and other motorized or power-based features within the system is operably attached. The plurality of modular units are tiered for movement that allows for custom access to each fixed tier and modular configurations by adding or removing additional selectable starting and stopping points based on the tier configuration(s). The motor or actuator controls one or more of a screw drive, a hydraulic pump, gear driven, a pulley system, or a belt system for actuating the modular tiers. The plurality of fixed modular units can also include customizable power ports accessible to the user.

A modular shelving system of the present disclosure provides another illustrative aspect. For example, a structural framework can support the weight of the modular shelving system. A plurality of tiered units are configured to allow for preconfigured customizable shelving configurations within the fixed tier structural framework. A motor for moving the plurality of tiered units within the structural framework can be actuated in response to user, controller or mechanical input. A controller for controlling the motor and stopping point within the plurality of tiered can be operably configured. The structural framework is designed to accommodate a variety of lift motors utilizing one or more belt or lift configurations connected to the motor, which can be utilized in customizable locations including in a bottom or top portion or in a corner or side panel or as a drive within the structural framework, and wherein the plurality of tier units is controlled. The plurality of tiered units can move to user selectable start and stop points allowing for customizable tiered shelving access at the access point. The plurality of sensors and IOT implementations are configured to control tier lights, rear camera, micro movement detection, and user selectable start and stop points allowing for sensor and IOT enablement at each tier.

In another aspect of the disclosure includes a method for accessing enclosed modular tiered units. Provided is an enclosed storage unit having a plurality of modular tiers within the storage unit accessible through an access point bay, an actuator operably connected to the plurality of modular tiers, and an actuator controller operably connected to the actuator wherein the actuator controller has one or more pre-programmed, user activated and deactivated start and stop positions associated with each of the plurality of modular tiers. User input can be received at the actuator controller for the one or more pre-programmed, user activated and deactivated start and stop positions. A tier can be selected from the plurality of modular tiers to be accessed in response to the user input. And, the selected tier can be actuated by the actuator from a raised or lowered position to the access point bay in response to a control signal from the actuator controller. The method can also include determining activation and deactivation of the one or more pre-programmed, user activated and deactivated start and stop positions for each of the plurality if modular tiers with a control switch operably connected to the actuator controller. Another inclusion can be activating the actuator with the actuator controller for moving the selected tier to the activated stop position and past the deactivated stop positions. One or more electronics 140 can be powered at each of the plurality of modular tiers through an electrical connection at each of tiers. Reconfiguring the plurality of modular tiers and updating the one or more pre-programmed, user activated and deactivated start and stop positions can be to correspond with the reconfigured plurality of modular tiers. Reconfiguring the plurality of modular tiers can be by uncoupling an existing tier from the plurality of modular tiers and/or coupling another tier to the plurality of modular tiers. Actuating horizontally with the actuator controller a shelf between non-extended and extended positions is provided, wherein at least a portion of the shelf 118 is outside the enclosed storage unit in the extended position. Sending a control signal to the actuator controller from a sensor 142 disposed within the enclosed storage unit for automatically detecting when the selected tier is at the one or more pre-programmed, user activated and deactivated start and stop positions is also provided.

In another aspect, a smart storage system is disclosed. The system can include a fixed tier framework configured for storage and a plurality of modular units operably attached to the fixed tier framework in a user-controlled configuration. The plurality of modular units can be interchangeable. A motor can be operably attached to the fixed tier framework and a controller can be operably attached to the motor. A user interface of the controller 136 can be configured for receiving user input to control a position of the plurality of modular units for access by a user. At least one extendable surface can be configured in one of the plurality of modular units, wherein the extendable surface, such as a shelf 118, has an extended position outside the one of the plurality of modular units and the fixed tier framework by actuation of the motor. The controller 136 and/or user interface can be a wired device or a wireless device. An enclosure 120 can house the fixed tier framework. The enclosure having at least one opening providing an access point for accessing at least one of the plurality of modular units. The user interface can include a layout 144 of the user-controlled configuration, the access point, and one of the plurality of modular units disposed at the access point. The plurality of modular units can have a raised or a lowered position to align and provide access to a selected one of the plurality of modular units through the access point by actuation of a motor. One or more electrical ports at each of the plurality of modular units can be configured to be accessible to the user for powering electronic devices.

A modular shelving system is provided in aspects of the disclosure. The system includes a structural framework, a plurality of tiered shelving units housed within and operably attached for movement in at least two opposing directions relative to the structural framework, and an actuator operably attached to the plurality of tiered shelving units, wherein the motor moves the plurality of tiered shelving units in the at least two opposing directions relative to the framework. The system can include an electronic controller operably connected to the actuator and an electronic controller interface having one or more controls for activating the actuator in the at least two opposing directions for controlling a position of the plurality of tiered shelving units relative to the framework. The system can also include an enclosure housing the plurality of tiered shelving units and at least one opening in the enclosure comprising an access point for accessing at least one of the plurality of tiered shelving units. The at least two opposing directions for controlling a position of the plurality of tiered shelving units can be one or more user-selected start and stop points relative to a user access point into at least one of the plurality of tiered shelving units. A plurality of sensors and one or more IOT implementations can be in operable connection with the actuator and one or more onboard electronic features associated with each of the plurality of tiered shelving units.

Figure 16:
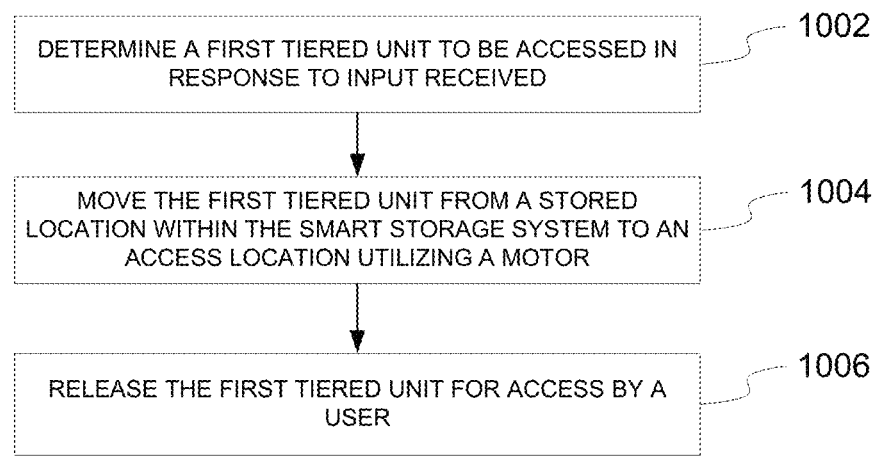
FIG. 16 is a flowchart of a process for utilizing the modular shelving system in accordance with an illustrative aspect.

FIG. 16 is a flowchart of a process for utilizing the modular shelving system in accordance with an illustrative aspect. In one aspect, the process of FIG. 10 may be implemented by a smart storage system as described herein. The smart storage system may include a number of tiered units. The tiered units may be movably connected to one or more motors utilizing belts, cables, chains, pulleys, slides, guides, tracks, or so forth. In one aspect, multiple columns of tiered units may be configured to move, vertically, cyclically, horizontally, or in any number of directions within the smart storage system. For example, a motor may move each of the tiered units within the smart storage system for access by one or more users. The motor may be controlled by a controller that interacts with a user through a user interface (e.g., buttons, switches, touchscreens, scroll wheels, knobs, etc.). In another aspect, the controller may also communicate with a transceiver configured to receive input through a wireless connection (e.g., direct, network based, etc.), network connection, or so forth.

The process may begin by determining a first tiered unit to be accessed in response to input received (step 1002). The tiered unit may store any number of products, goods, appliances, electronic devices 140 or so forth. In one aspect, the tiered unit may represent a workspace, such as a desk, cutting board, ironing board, working surface, or so forth. The workspace may be utilized by one or more users to perform any number of activities, actions, work, classes, or so forth. The input may represent instructions, commands, or feedback received directly from a user or indirectly from a device associated with the user (e.g., smart phone with a dedicated application, remote control, etc.). For example, the smart storage system may include an interface for receiving the input. The smart storage system may also receive the input through a wired connection, wireless signals, or so forth.

Next, the smart storage system moves the first tiered unit from a stored position to an access location utilizing a motor (step 1004). In one aspect, the stored position may represent a position or location of the first tiered unit that is inaccessible or unreachable to the user. For example, the first tiered unit may be stored behind other tiered units, above or below the user (e.g., inconvenient, inaccessible, etc.), or another locations or positions that otherwise require movement of the first tiered unit. In one aspect, the user may have specified heights, positions, or so forth for the access location. For example, the smart storage system may utilize different access positions for different users. The different access positions may be stored in user preferences, settings, parameters, or so forth. In another aspect, the smart storage system may utilize an optical system or other sensors to measure the height or size of the user for determining the access location. In one aspect, the access location may not only move the first tiered unit up and down within the smart storage system, but may also extend the first tiered unit horizontally or utilizing another motion (e.g., pivot, rotation, etc.).

Next, the smart storage system releases the first tiered unit for access by a user (step 1006). In one aspect, during step 1006, the smart storage system may lock or fix the first tiered unit at the access location. For example, this may ensure that the first tiered unit may be extended, electrically energized (e.g., available for power connections), or otherwise accessed by the user.

In other aspects, the smart storage system may activate products stored on the first tier. For example, an iron stored on the first tiered unit may be positioned and turned on to a specified temperature/setting. The smart storage system may also control secondary systems for activating devices, components, equipment, or performing any number of actions, processes, or so forth.

The illustrative aspects may take the form of an entirely hardware aspect, an entirely software aspect (including firmware, resident software, micro-code, etc.) or an aspect combining software and hardware aspects that may all generally be referred to herein as a "circuit," "module" or "system." Furthermore, aspects of the inventive subject matter may in part take the form of a computer program product embodied in any tangible medium of expression having computer usable program code embodied in the medium. The described aspects may be provided as a computer program product, or software, that may include a machine-readable medium having stored thereon instructions, which may be used to program a computing system (or other electronic device(s)) to perform a process according to aspects, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, aspects may be embodied in an electrical, optical, acoustical or other form of propagated signal (e.g., carrier waves, infrared signals, digital signals, etc.), or wireline, wireless, or other communications medium.

Computer program code for carrying out operations of the aspects may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 17:
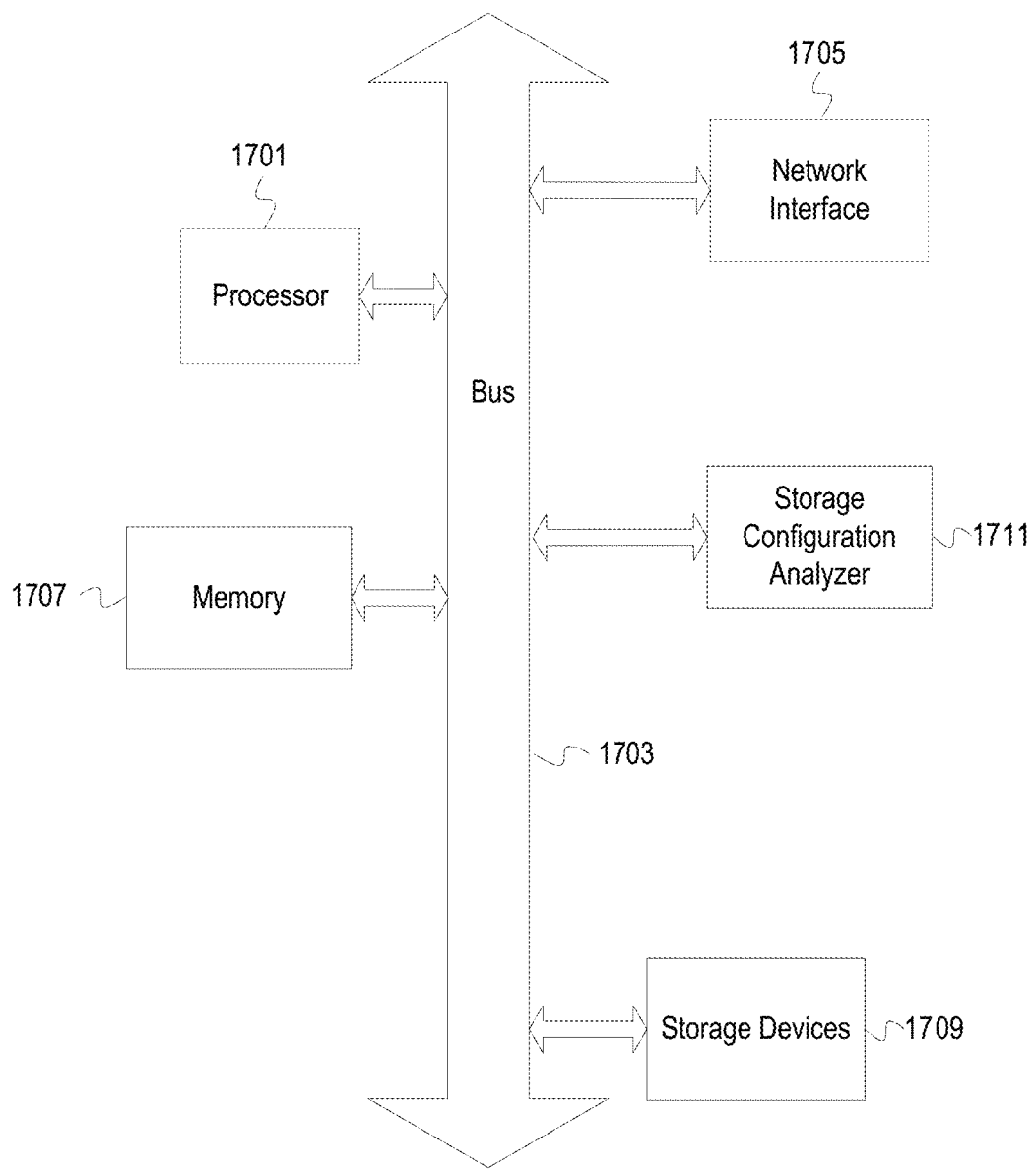
FIG. 17 is a pictorial representation of computing device controlling the smart storage system in accordance with an illustrative aspect.

FIG. 17 depicts a computing system 1700 in accordance with an illustrative aspect. For example, the computing system 1700 may represent a device, such as the wireless device 204 of FIG. 2. The computing system 1700 includes a processor unit 1701 (possibly including multiple processors, multiple cores, multiple nodes, and/or implementing multi-threading, etc.). The computing system includes memory 1707. The memory 1707 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 1703 (e.g., PCI, ISA, PCI-Express, HyperTransport®, InfiniBand®, NuBus, etc.), a network interface 1106 (e.g., an ATM interface, an Ethernet interface, a Frame Relay interface, SONET interface, wireless interface, etc.), and a storage device(s) 1709 (e.g., optical storage, magnetic storage, etc.). The system memory 1707 embodies functionality to implement all or portions of the aspects described above. The system memory 1707 may include one or more applications or sets of instructions for implementing a virtual assistant to communicate with one or more wireless earpieces. The virtual assistant may be stored in the system memory 1707 and executed by the processor unit 1702. As noted, the virtual assistant may be similar or distinct from a virtual assistant utilized by the wireless earpieces. Code may be implemented in any of the other devices of the computing system 1700. Any one of these functionalities may be partially (or entirely) implemented in hardware and/or on the processing unit 1701. For example, the functionality may be implemented with an application specific integrated circuit, in logic implemented in the processing unit 1701, in a co-processor on a peripheral device or card, etc. Further, realizations may include fewer or additional components not illustrated in FIG. 17 (e.g., video cards, audio cards, additional network interfaces, peripheral devices, etc.). The processor unit 1701, the storage device(s) 1709, and the network interface 1705 are coupled to the bus 1703. Although illustrated as being coupled to the bus 1703, the memory 1707 may be coupled to the processor unit 1701. The computing system 1100 may further include any number of optical sensors, accelerometers, magnetometers, microphones, gyroscopes, temperature sensors, and so forth for verifying user biometrics, or environmental conditions, such as motion, light, or other events that may be associated with the wireless earpieces or their environment.

The features, steps, and components of the illustrative aspects may be combined in any number of ways and are not limited specifically to those described. The illustrative aspects are not to be limited to the particular aspects and examples described herein. In particular, the illustrative aspects contemplate numerous variations in the type of ways in which aspects of the invention may be applied to smart storage, cabinet, drawer, and shelving devices and systems. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of aspects, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of aspects for implementing the invention and is not intended to be limiting in scope. The following claims set forth a number of the aspects disclosed with greater particularity.

What is claimed is:

1. A method for accessing enclosed modular tiered units, comprising:
   providing an enclosed storage unit configured to receive a plurality of modular tiers within the storage unit accessible through an access point bay, an actuator operably connected to the plurality of modular tiers, and an actuator controller operably connected to the actuator wherein the actuator controller has one or more pre-programmed, user activated and deactivated start and stop positions associated with each of the plurality of modular tiers;
   receiving a user selection of the plurality of modular tiers that are enabled to be added or removed from the enclosed storage unit by a user for customization;
   receiving user input at the actuator controller for the one or more pre-programmed, and user activated and deactivated start and stop positions;
   selecting a tier from the plurality of modular tiers to be accessed in response to the user input;
   actuating the selected tier with the actuator from a raised or lowered position to the access point bay in response to a control signal from the actuator controller.

2. The method of claim 1, further comprising:
   determining activation and deactivation of the one or more pre-programmed, user activated and deactivated start and stop positions for each of the plurality if modular tiers with a control switch operably connected to the actuator controller.

3. The method of claim 1, further comprising:
   activating the actuator with the actuator controller for moving the selected tier to the activated stop position and past the deactivated stop positions.

4. The method of claim 1, further comprising:
   powering one or more electronics at each of the plurality of modular tiers through an electrical connection at each of tiers.

5. The method of claim 1, further comprising:
   reconfiguring the plurality of modular tiers and updating the one or more pre-programmed, user activated and deactivated start and stop positions to correspond with the reconfigured plurality of modular tiers.

6. The method of claim 1, further comprising:
reconfiguring the plurality of modular tiers by:
uncoupling an existing tier from the plurality of modular tiers;
coupling another tier to the plurality of modular tiers.

7. The method of claim 1, further comprising:
actuating horizontally with the actuator controller a shelf between non-extended and extended positions, wherein at least a portion of the shelf is outside the enclosed storage unit in the extended position.

8. The method of claim 1, further comprising:
sending a control signal to the actuator controller from a sensor disposed within the enclosed storage unit for automatically detecting when the selected tier is at the one or more pre-programmed, user activated and deactivated start and stop positions.

9. A smart storage system, comprising:
a fixed tier framework configured for storage;
a plurality of modular units operably attached to the fixed tier framework in a user-controlled configuration, wherein a user selection of the plurality of modular units that are enabled to be added or removed from the enclosed storage unit by a user for customization is received;
a motor operably attached to the fixed tier framework;
a controller operably attached to the motor;
a user interface of the controller for receiving user input to control a position of the plurality of modular units for access by the user.

10. The smart storage system of claim 9, further comprising:
at least one extendable surface of one of the plurality of modular units, wherein the extendable surface has an extended position outside the one of the plurality of modular units and the fixed tier framework by actuation of the motor.

11. The smart storage system of claim 9, wherein the user interface comprises a wired device or a wireless device.

12. The smart storage system of claim 9, further comprising:
an enclosure housing the fixed tier framework, the enclosure having at least one opening providing an access point for accessing at least one of the plurality of modular units.

13. The smart storage system of claim 12, wherein the user interface includes a layout of the user-controlled configuration, the access point, and one of the plurality of modular units disposed at the access point.

14. The smart storage system of claim 12, wherein the plurality of modular units have a raised or a lowered position to align and provide access to a selected one of the plurality of modular units through the access point by actuation of the motor.

15. The smart storage system of claim 9, further comprising:
one or more electrical ports at each of the plurality of modular units accessible to the user for powering electronic devices.

16. A modular shelving system, comprising:
a structural framework;
a plurality of tiered shelving units housed within and operably attached for movement in at least two opposing directions relative to the structural framework, wherein a user selection of the plurality of tiered shelving units that are enabled to be added or removed by a user for customization is received; and
an actuator operably attached to the plurality of tiered shelving units, wherein the motor moves the plurality of tiered shelving units in the at least two opposing directions relative to the framework.

17. The modular shelving system of claim 16, further comprising:
an electronic controller operably connected to the actuator and an electronic controller interface having one or more controls for activating the actuator in the at least two opposing directions for controlling a position of the plurality of tiered shelving units relative to the framework.

18. The modular shelving system of claim 16, further comprising:
an enclosure housing the plurality of tiered shelving units and at least one opening in the enclosure comprising an access point for accessing at least one of the plurality of tiered shelving units.

19. The modular shelving system of claim 16, wherein the at least two opposing directions for controlling a position of the plurality of tiered shelving units comprise one or more user-selected start and stop points relative to a user access point into at least one of the plurality of tiered shelving units.

20. The modular shelving system of claim 16, further comprising:
a plurality of sensors and one or more IOT implementations in operable connection with the actuator and one or more onboard electronic features associated with each of the plurality of tiered shelving units.

* * * * *